US00PP34374P2

(12) United States Plant Patent
Manly et al.

(10) Patent No.: US PP34,374 P2
(45) Date of Patent: Jun. 28, 2022

(54) APPLE TREE NAMED 'D27-16'

(50) Latin Name: *Malus domestica*
Varietal Denomination: Regal 'D27-16'

(71) Applicant: Regal Fruit International, LLC, Ephrata, WA (US)

(72) Inventors: Neal Manly, Ephrata, WA (US); Kenneth Adams, Ephrata, WA (US)

(73) Assignee: Regal Fruit International, LLC, Ephrata, WA (US)

( * ) Notice: Subject to any disclaimer, the term of this patent is extended or adjusted under 35 U.S.C. 154(b) by 0 days.

(21) Appl. No.: 17/300,016

(22) Filed: Feb. 9, 2021

(51) Int. Cl.
*A01H 5/02* (2018.01)
*A01H 6/74* (2018.01)

(52) U.S. Cl.
USPC ..... Plt./172
CPC ..... *A01H 6/7418* (2018.05)

(58) Field of Classification Search
USPC ..... Plt./172
CPC ..... A01H 6/7418
See application file for complete search history.

*Primary Examiner* — Anne Marie Grunberg
(74) *Attorney, Agent, or Firm* — Lee & Hayes, P.C.

(57) ABSTRACT

A new and distinctive variety of *Malus domestica* apple tree from a controlled cross of '8S6923' (application Ser. No. 11/003,323), now abandoned, x 'Honeycrisp' (U.S. Plant Pat. No. 7,197P) that is distinctly different from its parents and other mid-season apples.

6 Drawing Sheets

Latin name: *Malus domestica.*
Varietal denomination: Regal 'D27-16'.

BACKGROUND

The present invention relates to a new, novel, and distinct variety of apple tree, and which has been denominated varietally as 'D27-16,' and more specifically, to a novel apple tree with an upright growth habit with moderate vigor. The novel apple tree produces a unique golden fruit that exhibits uniform skin color when mature, and whose lenticels are not raised and nearly indistinct. The flesh is very firm and quite sweet with a moderate tartness. The fruit when cut is slow to brown and lite in degree. The tree is a spur type and is a tip bearer.

ORIGIN AND ASEXUAL REPRODUCTION

It has long been recognized that an important factor contributing to the success of a new variety of apple tree bearing fresh market fruit is its growing characteristics as well as characteristics of its fruit. Another significant factor affecting the commercial viability of a new variety of apple relates to its storage characteristics, and which are reflected by pomological traits such as fruit pressure and soluble solids to name but a few.

The new variety of apple tree described herein was derived by the following methodology.

The new variety 'D27-16' was asexually reproduced in Quincy, Wash. For example, 'D27-16' was derived by a controlled pollination of '8S6923' (application Ser. No. 11/003,323) with the pollen of 'Honeycrisp' (U.S. Plant Pat. No.7,197) in the spring of 2008. Seeds from this cross were collected in the spring of 2009. Seedlings grew for two seasons, after which buds from each seedling were budded onto M9 rootstock. In the spring of 2012, the seedlings were planted in a research plot located near 3560 RD 5 NW, Ephrata, Wash. 98823. Fruit from these trees were observed in the fall of 2013, and 'D27-16' was selected. Second generation trees were budded onto M9 and planted in the spring of 2014 at 9761 Road U NW, Quincy, Wash., 98848. Fruit generated from the second-generation trees have been studied and compared and it appears that all characteristics of the subsequent asexually reproductive trees remain true to that seen in the original first generation tree.

SUMMARY OF NEW VARIETY

The 'D27-16' apple tree is characterized as to novelty by its distinctive traits from its parent varieties, '8S6923' (application Ser. No. 11/003,323) and 'Honeycrisp' (U.S. Plant Pat. No.7,197P). By way of example, 'D27-16' exhibits spur-type characteristics, exhibits upright growth habit with moderate vigor as grown on M9 rootstock, is a mid-season bloomer and will allow for pollination from any other diploid apple of the same bloom season. Fruit at maturity has a unique and uniform golden color, whose lenticels are not raised and nearly indistinct. The flesh of 'D27-16' is very firm and quite sweet with a moderate tartness. Then cut, the fruit is slow to brown and is lite in degree. The fruit exhibits 3+ months of common storage life.

'D27-16' is distinct from its female parent, '8S6923' (application Ser. No. 11/003,323). For example, both the 'D27-16' and '8S6923' produce juicy fruit best used for dessert that is firm and sweet, and has an excellent shelf life. Both 'D27-16' and '8S6923' hive a high productivity and are considered hardy. However, the shape of the 'D27-16' is flat slender code and generally spur and tip bearing habit, while '8S6923' is spreading and mainly spur bearing.

The closest known antecedent to 'D27-16' is the 'Honeycrisp' (U.S. Plant Pat. No.7,197P). The following are some characteristics to distinguish 'D27-16' from the 'Honeycrisp.' 'D27-16' and 'Honeycrisp' are both upright with smooth bark. However, the lenticels of 'D27-16' are significantly smaller than those of the 'Honeycrisp,' which exhibits prominent lenticels. The 'D27-16' leaf is smaller, both in length and width, than the leaf of the 'Honeycrisp.' The fruit of 'D27-16' is smaller in diameter than the 'Honeycrisp,' but both the 'D27-16' and the 'Honeycrisp' have crisp and juicy flesh.

The closest known antecedent to 'D27-16' that is not a parental variety is the 'Golden Delicious' (unpatented). Both 'D27-16' and 'Golden Delicious' exhibit similar fruit taste, fruit shape and yellow color of fruits. However, the fruit of 'D27-16' is very firm, while the skin of 'Golden Delicious' is prone to bruising and shriveling.

BRIEF DESCRIPTION OF DRAWINGS

The accompanying drawings are color photographs of the present variety.

NOT A COMMERCIAL WARRANTY

Figure 1:
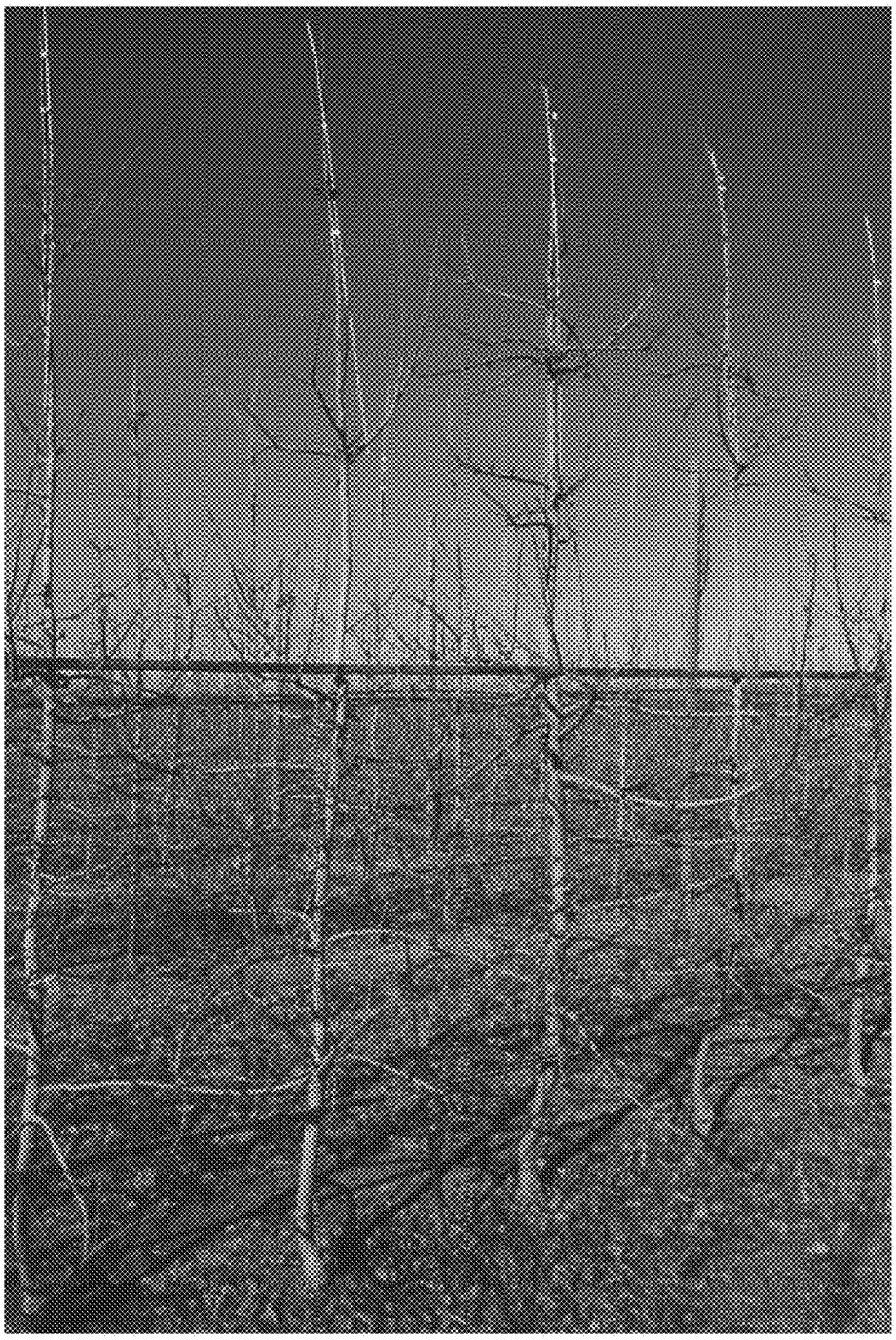
FIG. 1 depicts a dormant second generation 'D27-16' tree.
Figure 2:
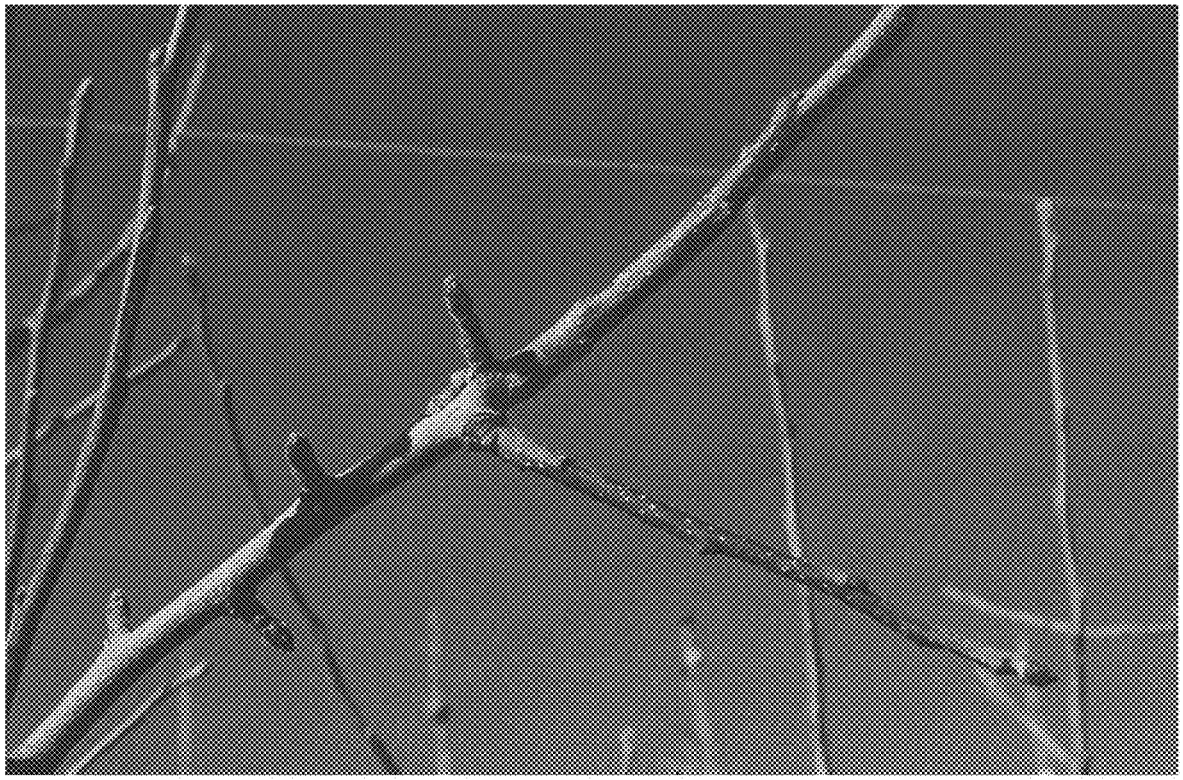
FIG. 2 depicts spur development of a second generation 'D27-16' tree.
Figure 3:
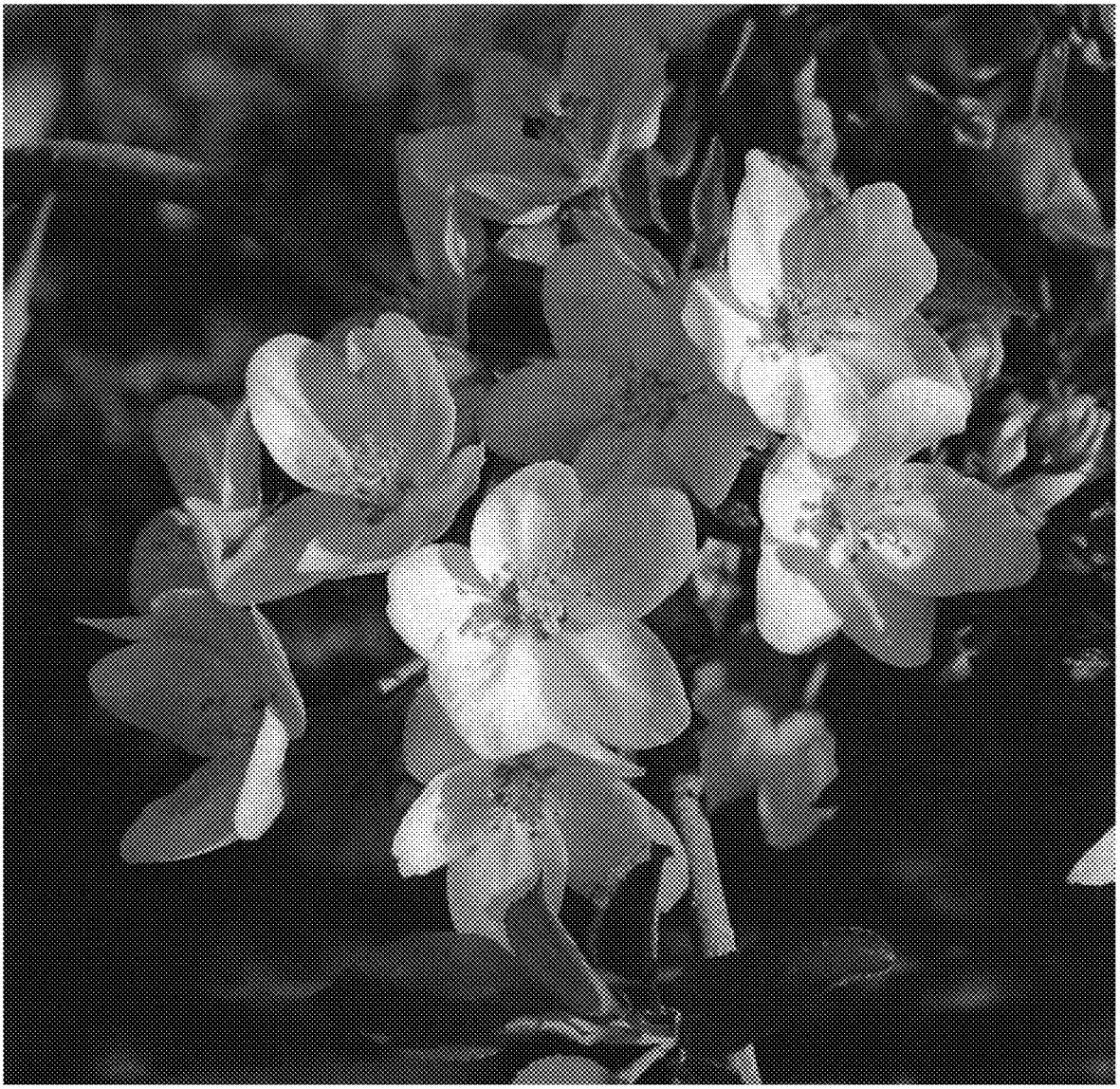
FIG. 3 depicts a typical blossom cluster of 'D27-16' at full bloom.
Figure 4:
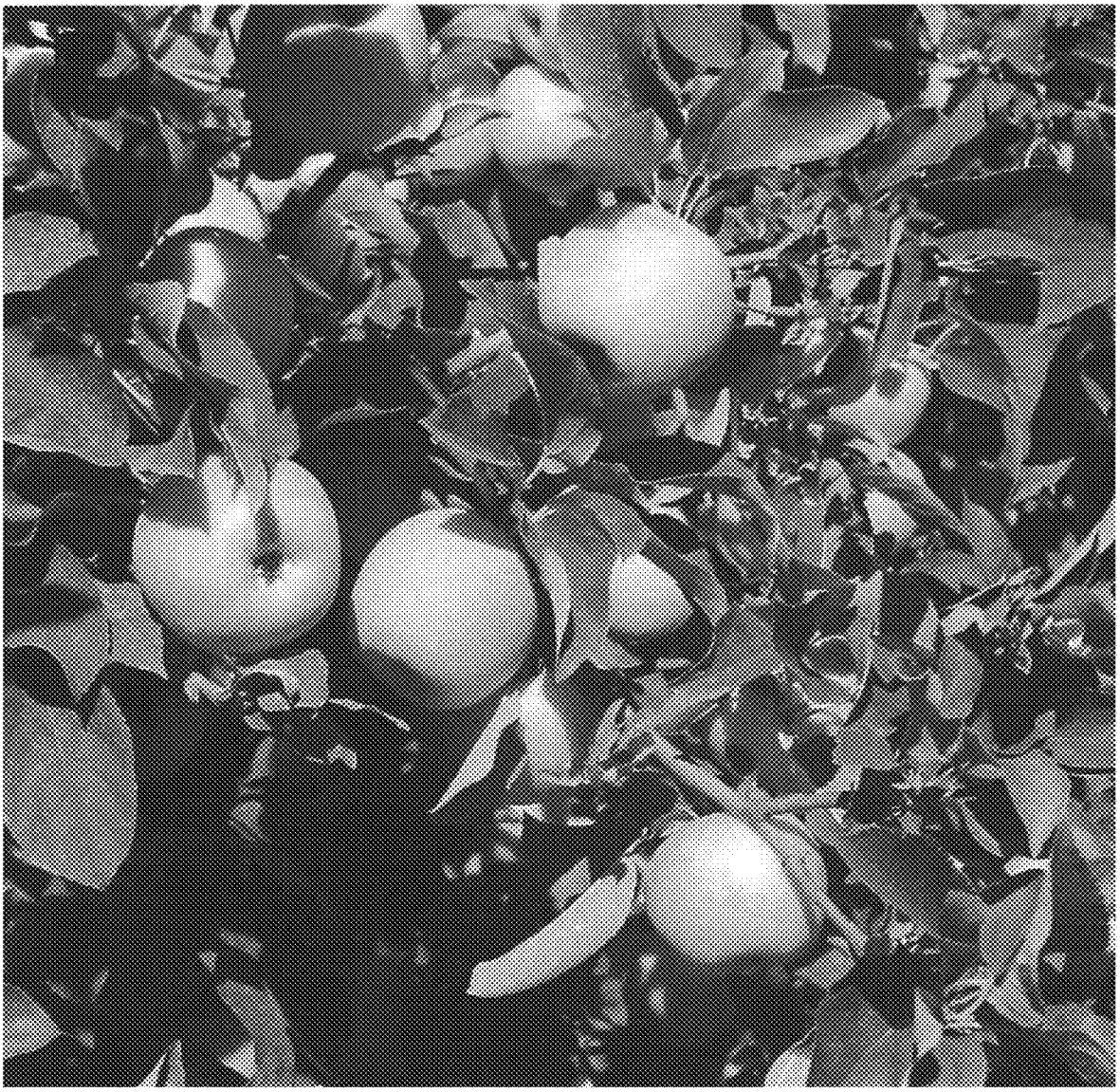
FIG. 4 depicts a fruiting limb of 'D27-16' at pre-harvest.
Figure 5:
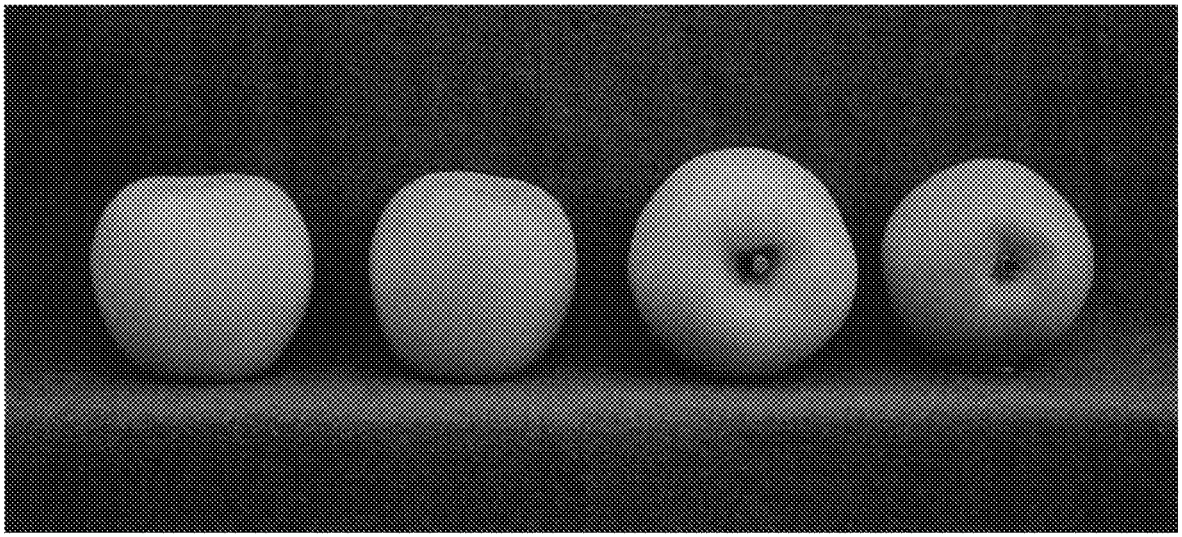
FIG. 5 illustrates four positions of harvest-mature 'D27-16' fruit.
Figure 6:
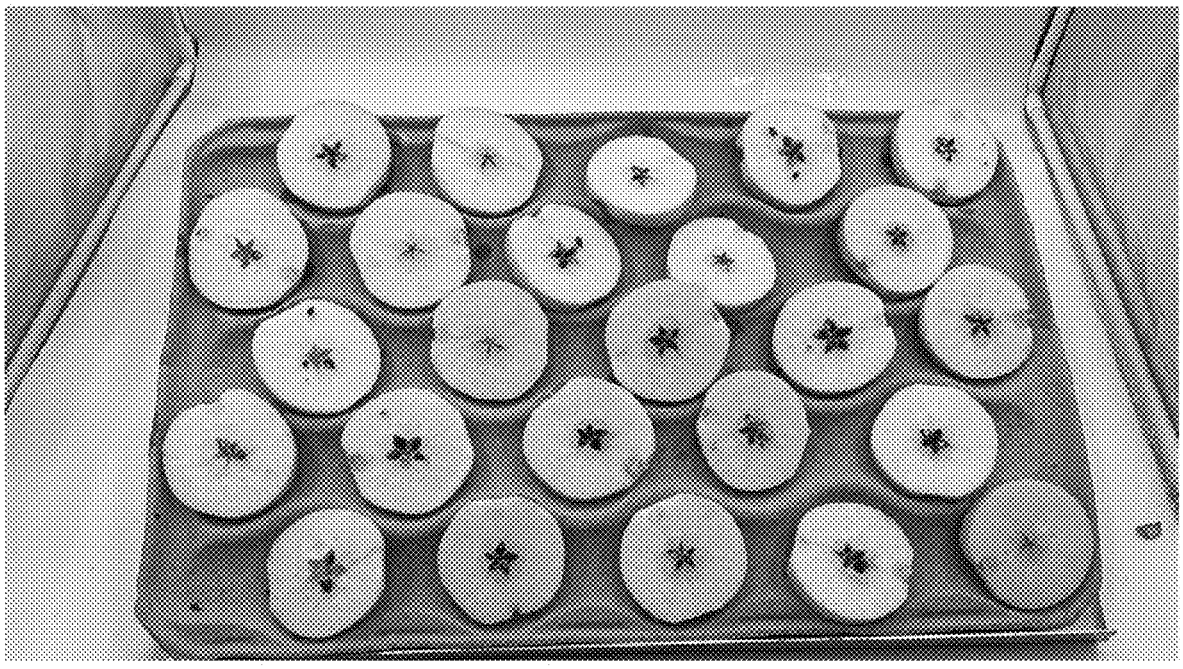
FIG. 6 illustrates multiple "D27-16" fruit transversely sliced.

The following detailed description has been prepared to solely comply with the provisions of 35 U.S.C. § 112, and does not constitute a commercial warranty, (either expressed or implied), that the present variety will, in the future, display the botanical, pomological or other characteristics as set forth herein. Therefore, this disclosure may not be relied upon to support any future legal claims, including but not limited to breach of warranty of merchantability, or fitness for any particular purpose, which is directed, in whole, or in part, to the present variety.

DETAILED DESCRIPTION

Referring more specifically to the pomological and botanical details of this new and distinct variety of apple tree, the following has been observed from six-year-old second-generation trees grown at 3135 Warehouse Rd., Wenatchee, Wash. 98801, USDA Hardiness Zone 6A, and asexually reproduced at 3560 Road 5 NW, Ephrata, Wash. 98823, Hardiness Zone 6A. All color references are from The RHS Colour Chart by The Royal Horticulture Society.

TREE

Tree type: The present variety is a 6 wire espalier.

Tree vigor: Considered moderate.

Tree shape: Flat slender cone.

Tree height: The present variety, when measured during its ninth leaf, has an overall height of about nine feet.

Tree width: As measured during the ninth leaf, the new tree exhibits a width of about three feet.

Hardiness: Considered hardy for the North Central Washington region.

Fruit productivity: Considered moderately high for the species.

TRUNK

Trunk diameter: About 6.1 centimeters when measured at a height of about 30 centimeters above the ground.

Bark texture: Smooth.

Bark color: From the Greyed-Brown group (RHS 199A).

Trunk lenticels: Generally present and averaging about 13 lenticels per nine centimeter square area.

Trunk lenticel width: Generally from about 0.5 millimeters to about 0.6 millimeters.

Trunk lenticel length: Generally from about 2.4 millimeters to about 3.9 millimeters with an average of about 3.1 millimeters.

Trunk lenticel color: From the Greyed-Orange group (RHS N163C).

Trunk lenticel shape: Generally flat.

BRANCHES

Scaffold branches:

Scaffold branch diameter: From about 12.8 centimeters to about 19.2 centimeters with an average of 15.4 centimeters as measured at 10 centimeters from trunk.

Scaffold branch length: From about 52.5 centimeters to about 75.0 centimeters when an average of about 63.5 centimeters.

Scaffold branch color: From the Greyed-Brown group (RHS 199A).

Scaffold branch texture: Generally smooth.

Scaffold branch lenticels: Generally averaging about 36 lenticels per nine centimeter square area.

Scaffold branch lenticel Shape: Some round, mostly flat.

Scaffold branch lenticel Length: Generally from about 1.8 millimeters to about 2.9 millimeters with an average of about 2.2 millimeters.

Scaffold branch lenticel width: Generally from about 0.3 millimeters to about 0.5 millimeters.

Scaffold branch lenticel color: Generally from the Greyed-Orange group (RHS N163C).

Two-year-old fruiting branches:

Two-year-old branch diameter: From about 5.4 millimeters to about 9.2 millimeters with an average of about 7.5 millimeters.

Two-year-old branch length: From about 7.5 centimeters to about 30.0 centimeters with an average of about 14.8 centimeters.

Two-year-old branch texture: Smooth.

Two-year-old branch color: From the Greyed-Orange group (RHS 165A).

Two-year-old branch pubescence: None.

Two-year-old branch lenticel numbers: Averaging about 22 lenticels per running centimeter of surface area.

Two-year-old branch lenticel shape: Generally round.

Two-year-old branch lenticel diameter: From about 0.5 millimeters to about 0.7 millimeters.

Two-year-old branch lenticel color: From the Greyed-Orange group (RHS 164B).

Two-year-old branch spur development:

Two-year-old branch spur development: Generally spur and tip bearing habit present.

Two-year-old branch spur length: From about 6.4 millimeters to about 12.0 millimeters with an average of about 8.6 millimeters.

Two-year-old branch diameter: From about 5.4 millimeters to about 9.2 millimeters with an average of about 7.5 millimeters.

Two-year-old branch bud shape: Generally more globose than elliptical.

Two-year-old branch spur bud length: From about 5.5 millimeters to about 8.4 millimeters with an average of about 6.7 millimeters.

Two-year-old branch spur bud diameter: From about 3.2 millimeters to about 4.0 millimeters with an average of about 3.7 millimeters.

Two-year-old branch bud scale color: From the Greyed-Purple group (RHS 183A).

Two-year-old branch spur pubescence: Light in density and present on tips only.

Two-year-old branch spur pubescence color: From the White group (RHS N155D).

Two-year-old internode length: From about 1.9 centimeters to about 3.8 centimeters with an average of about 2.6 centimeters.

Two-year-old branch crotch angle: Ranging from about 45 degrees to about 80 degrees.

2020 Branches:

2020 branch texture: Generally Smooth.

2020 branch length: From about 16.5 centimeters to about 32.5 centimeters with an average of about 23.7 centimeters.

2020 branch diameter at midpoint: From about 3.1 millimeters to about 4.8 millimeters with an average of about 3.8 millimeters.

2020 branch pubescence: Present and light in density covering about 50-80% of surface area.

2020 branch pubescence color: From the White group (RHS 155C).

2020 branch bark color: From the Greyed-Purple group (RHS 183A).

2020 branch lenticels: Present and averaging about 18 per running centimeter of branch.

2020 branch lenticel shape: Generally round.

2020 branch lenticel diameter: From about 0.2 millimeters to about 0.8 millimeters.

2020 branch lenticel color: From the white group (RHS 155A).

2020 branch internode length: From about 2.4 millimeters to about 3.4 millimeters with an average of about 2.9 millimeters.

BLOOM (FLOWERS)

Date of first bloom: Apr. 14, 2020.

Date of full bloom: Apr. 19, 2020.

Bud shape: More globose than elliptical.

Bud Length: Ranging from about 5.5 millimeters to about 8.4 millimeters with an average of about 6.7 millimeters.

Vegetative bud support diameter: Ranging from about 2.4 millimeters to about 5.5 millimeters with an average of about 3.8 millimeters.

Number of blossoms per bud: From about 4 to 6, mostly 5.

Blossom size: Generally considered medium large.

Diameter when fully open: Ranging from about 4.6 centimeters to about 5.5 centimeters with an average of about 5.1 centimeters.

Petal count: About 5 per blossom.

Petal arrangement: Slight overlap when fully open.

Petal shape: Round oblong to oblong.

Petal tip shape: Rounded.

Petal tip base: Rounded with an occasional cordate.

Petal width: Ranging from about 4.6 centimeters to about 5.5 centimeters with an average of about 5.1 centimeters.

Petal length: Ranging from about 20.5 millimeters to about 26.0 millimeters with an average of about 23.3 millimeters.

Petal color unopened: 80% of surface area from the Red-Purple group (RHS 60C). Remainder from the White group (RHS N155D).

Petal color opened: 70% of both upper and lower surfaces from the White group (RHS N155D). Remaining 30% of both upper and lower surfaces from the Red-Purple group (RHS N74C).

Stamen number: Ranging from about 16 to about 20 with an average of about 18.

Stamen filament length: From about 3.8 millimeters to about 9.3 millimeters with an average of about 6.7 millimeters.

Stamen filament color: From the White group (RHS 155C).

Stamen anthers shape: Generally more Heart shaped than Kidney shaped.

Stamen anthers width: From about 1.4 millimeters to about 1.9 millimeters with an average of about 1.7 millimeters.

Stamen anthers length: From about 1.8 millimeters to about 2.7 millimeters with an average of about 2.3 millimeters.

Stamen anthers color: From the White group (RHS 155A).

Stamen anthers pollen: Generally considered moderate in density.

Stamen anthers pollen color: From the Greyed-Orange group (RHS 164A).

Pistil style: About 5 in number.

Pistil length: From about 10.3 millimeters to about 12.9 millimeters with an average of about 11.2 millimeters. Branches are fused at an average of about 3.2 millimeters from base.

Pistil color: From the Yellow-Green group (RHS 145A). Fused section from the Greyed-Green group (RHS 197B).

Pubescence: None.

Stigma number: About 5 per blossom.

Stigma shape: Generally Club.

Stigma color: From the Yellow-Green Group (RHS 153A).

Sepal: moderately curled towards peduncle.

Septal number: About 5 per blossom.

Sepal shape: Generally Lanceolate.

Sepal shape at tip: Narrowly Acute.

Sepal shape at base: Generally Flat (truncate).

Sepal length: From about 9.1 millimeters to about 11.5 millimeters with an average of about 10.3 millimeters.

Sepal width: From about 3.3 millimeters to about 4.5 millimeters with an average of about 3.9 millimeters.

Septal margin: Smooth.

Sepal color: From the Green group (RHS 138A).

Sepal pubescence: Present and abundant on both upper and lower surfaces.

Sepal pubescence color: From the White group (RHS 155C).

Peduncle length: From about 8.3 millimeters to about 16.8 millimeters with an average of about 13.4 millimeters.

Peduncle diameter at midpoint: From about 1.1 millimeters to about 1.6 millimeters with an average of about 1.4 millimeters.

Peduncle color: From the Yellow-Green Group (RHS 144A).

Peduncle pubescence: Abundant over 100% of surface area.

Peduncle pubescence color: From the White group (RHS 155C).

Thalmus depth: From about 1.3 millimeters to about 2.6 millimeters with an average of about 2.0 millimeters.

Thalmus diameter: From about 2.2 millimeters to about 3.7 millimeters with an average of about 2.9 millimeters.

Thalmus color: From the Yellow-Green group (RHS 144A).

Nectary color: From the Yellow-Green group (RHS 146A).
Thalmus pubescence: Moderate and covering 100% of the outer surface.
Thalmus pubescence color: From the White group (RHS 155C).

LEAVES

Shape: Generally broadly acute.
Upper texture: Generally smooth and leathery.
Lower texture: Generally smooth with veins protruding below the surface.
Upper sheen: Smooth and leathery with bright sheen.
Lower sheen: Moderately dull sheen.
Pubescence: Present and moderate in density over 100% of surface.
Pubescence color: From the White group (RHS 155C).
Length: From about 8.7 centimeters to about 10.1 centimeters with an average of about 9.5 centimeters.
Width: From about 5.4 centimeters to about 7.9 centimeters with an average of about 6.0 centimeters.
Margin: Generally serrate.
Tip: Generally cuspidate.
Leaf blade tip length: Averaging about 1.2 millimeters.
Base: Generally rounded.
Upper blade color: From the Yellow-Green group (RHS 147A).
Lower blade color: From the Yellow-Green group (RHS 147B).
Stipules: Generally present from about 0 to 2 per leaf.
Stipules shape: Generally small linear.
Stipules length: From about 3.2 millimeters to about 5.5 millimeters with an average of about 4.6 millimeters.
Stipules width: From about 0.7 millimeters to about 1.0 millimeters with an average of about 0.8 millimeters.
Stipules color: From the Yellow-Green group (RHS 144D).
Stipules pubescence: None.
Stipules mid vein diameter at midpoint: From about 1.3 millimeters to about 1.7 millimeters with an average of about 1.5 millimeters.
Stipules mid vein color: Both upper and lower from the Yellow-Green Group (RHS 145D).
Stipules mid vein pubescence: Present on lower surface and moderate in density over 100% of surface.
Stipules mid vein pubescence color: From the White group (RHS 155C).
Petiole: Generally full length shallow grove upper surface.
Petiole length: From about 2.7 centimeters to about 3.6 centimeters with an average of about 3.2 centimeters.
Petiole diameter at midpoint: From about 1.3 millimeters to about 1.7 millimeters with an average of about 1.5 millimeters.
Petiole upper surface color: From the Yellow-Green group (RHS 145C).
Petiole under surface color: From the White group (RHS 155C). Basal end from the Green-Red group (RHS 181A).
Petiole pubescence: Generally moderate in density over 100% of surface area.
Petiole pubescence color: From the White group (RHS 155C).
Petiole attitude: Not downward hanging.

FRUIT

Generally: The observations which follow have been taken from the first-generation tree fruit.
Form: Considered round-conical.
Equatorial diameter: From about 7.5 centimeters to about 8.2 centimeters with an average of about 7.9 centimeters.
Axis diameter: From about 6.6 centimeters to about 7.5 centimeters with an average of about 7.1 centimeters.
Stem: Generally short, stalky, and clubbed.
Stem length: From about 12.8 millimeters to about 20.4 millimeters with an average of about 16.1 millimeters.
Stem diameter at midpoint: From about 2.1 millimeters to about 4.5 millimeters with an average of about 3.2 millimeters.
Stem color: From the Yellow-Green group (RHS 145C).
Stem pubescence: Present and moderate in density over 100% of the surface area.
Stem pubescence color: From the White group (RHS 155C).
Stem cavity shape: Generally acute.
Stem cavity lipped: No
Stem cavity russet: Generally very lite to none.
Stem cavity russet color: From the Greyed-Yellow group (RHS 162D).
Stem cavity width: From about 3.1 centimeters to about 3.7 centimeters with an average of about 3.4 centimeters.
Stem cavity depth: From about 1.8 centimeters to about 2.2 centimeters with an average of about 2.1 centimeters.
Basin cavity shape: Considered urn shaped and lightly 5 crowned.
Basin cavity ribbed: Yes.
Basin cavity sides: Considered smooth.
Basin cavity width: From about 3.1 centimeters to about 3.7 centimeters with an average of about 3.4 centimeters.
Basin cavity depth: From about 1.8 centimeters to about 2.4 centimeters with an average of about 2.1 centimeters.
Basin cavity eye: Sepals erect and open.
Basin cavity eye color: From the Greyed-Yellow group (RHS 162D).
Basin cavity eye pubescence: Present over 100% of both sides, lite in density.
Basin cavity eye pubescence color: From the White group (RHS 155C).
Basin cavity eye shape: Urn shaped and lightly 5 crowned.
Skin appearance: 100% Flush.
Skin color: From the Yellow group (RHS 3C).
Skin thickness: Considered thin, 0.01 millimeters.
Skin texture: Generally smooth.
Skin lenticels: Present with greater numbers at apex. Lenticels are not raised and nearly indistinct.
Skin lenticels shape: Generally round.
Skin lenticels diameter: From about 0.1 millimeters to about 0.5 millimeters.
Skin lenticels number at apex: About 9 per square centimeter.
Skin lenticels Number at shoulder: About 5 per square centimeters.
Core position: Considered distant.
Core line position: Meeting.
Core shape: Generally short, round conical.
Core length: From about 2.2 centimeters to about 2.5 centimeters with an average of about 2.4 centimeters.
Core diameter: From about 3.2 centimeters to about 3.5 centimeters with an average of about 3.3 centimeters.
Cell tufted: Considered spotty over 20-30% of the inner surface.
Cell shape: Elliptical.
Cell length: From about 12.8 millimeters to about 15.3 millimeters with an average of about 14.1 millimeters.

Cell width: From about 3.5 millimeters to about 4.9 millimeters with an average of about 4.2 millimeters.
Cell wall-to-wall distance: From about 3.5 millimeters to about 4.9 millimeters with an average of about 4.2 millimeters.
Tube shape: Considered cone shaped.
Tube stamen position: Considered basal.
Tube axis: Considered closed axile.
Seed number: 2-3 per cell.
Seed shape: Considered obtuse.
Seed length: From about 6.4 millimeters to about 7.2 millimeters with an average of about 6.8 millimeters.
Seed width: From about 3.8 millimeters to about 4.9 millimeters with an average of about 4.4 millimeters.
Seed depth (wall to wall): From about 2.3 millimeters to about 3.0 millimeters with an average of about 2.7 millimeters.
Seed color: From the Greyed-Orange group (RHS 177A).
Flesh: Crisp and juicy with a melting skin. Exhibits lite browning 30 minutes following cutting.
Flesh color: From the Yellow group (RHS 12D).
Aroma: Faint apple-like.
Date of harvest maturity: Sep. 16, 2020.
Maturity pressure: Averages 20.0#.
Maturity starch: 3.5 as determined from the golden delicious starch chart.
Maturity soluble solids: 15.2 brix.
Maturity malic acid: 0.5 as percent malic acid.
Keeping quality: Excellent. 3+ Months in common storage.
Productivity: Considered moderately high.
Pollination: Occurs with early bloom timing varieties lacking S9 or S24 alleles.
Use: Dessert, juice, drying.
Disease and insect resistance: Considered to be susceptible to all insects and diseases found in the region of Central Washington. Fruit does not exhibit any physiological disorders on the tree nor during storage for the duration of normal storage lengths. Regal 'D27 16' has undergone virus screen in 2017 by Phytelligence and found to be free of the 12 viruses recommended for testing by the National Clean Plant Network (NCPN).

Although the new variety of apple tree possesses the described characteristics when grown under the ecological conditions prevailing in Quincy, Wash., in the south-central part of Washington state, it should be understood that variations of the usual magnitude and characteristics incident to changes in growing conditions, fertilization, pruning and pest control as well as horticultural management practices are to be expected.

What is claimed is:

1. A new and distinct variety of Apple tree named Regal 'D27-16' as herein illustrated and described.

* * * * *